(12) United States Patent
Friesz et al.

(10) Patent No.: US 8,501,971 B2
(45) Date of Patent: Aug. 6, 2013

(54) PROCESS FOR THE PREPARATION OF DRONEDARONE

(75) Inventors: Antal Friesz, Budapest (HU); Zsolt Dombrady, Budapest (HU); Mariann Csatarine Nagy, Budapest (HU)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/479,615

(22) Filed: May 24, 2012

(65) Prior Publication Data

US 2012/0289717 A1 Nov. 15, 2012

Related U.S. Application Data

(63) Continuation of application No. PCT/HU2010/000128, filed on Nov. 23, 2010.

(30) Foreign Application Priority Data

Dec. 8, 2009 (HU) ...................................... 0900759

(51) Int. Cl.
*C07D 307/78* (2006.01)
(52) U.S. Cl.
USPC ............................. 549/488; 549/429; 549/483
(58) Field of Classification Search
USPC ......................................... 549/429, 483, 488
See application file for complete search history.

(56) References Cited

U.S. PATENT DOCUMENTS

| | | | |
|---|---|---|---|
| 5,223,510 A | 6/1993 | Gubin et al. | |
| 6,828,448 B2 | 12/2004 | Fino et al. | |
| 6,846,936 B2 | 1/2005 | Biard | |
| 6,984,741 B2 * | 1/2006 | Magerlein | 549/466 |
| 7,312,345 B2 * | 12/2007 | Gutman et al. | 549/466 |
| 2012/0065411 A1 | 3/2012 | Kretzschmar et al. | |
| 2012/0077995 A1 | 3/2012 | Kretzschmar et al. | |
| 2012/0330036 A1 | 12/2012 | Friesz et al. | |

FOREIGN PATENT DOCUMENTS

| | | |
|---|---|---|
| EP | 0471609 A1 | 2/1992 |
| EP | 1394155 A2 | 3/2004 |
| WO | WO 02/48078 A1 | 6/2002 |
| WO | WO 02/48132 A1 | 6/2002 |
| WO | WO 03/040120 A1 | 5/2003 |
| WO | WO 03/048144 A2 | 6/2003 |
| WO | WO 2012/010788 | 1/2012 |
| WO | WO 2012/010802 | 1/2012 |
| WO | WO 2012/010913 | 1/2012 |
| WO | WO 2012/127173 | 9/2012 |
| WO | WO 2012/131408 | 10/2012 |
| WO | WO 2012/131409 | 10/2012 |
| WO | WO 2012/131410 | 10/2012 |

OTHER PUBLICATIONS

International Search Report for WO2011/070380 dated Jun. 16, 2011.
U.S. Appl. No. 13/599,374, filed Aug. 30, 2012, Bailly, et al.
U.S. Appl. No. 13/638,484, filed Aug. 30, 2012, Bailly, et al.
U.S. Appl. No. 13/638,500, filed Sep. 28, 2012, Priem, et al.
U.S. Appl. No. 13/628,867, filed Sep. 27, 2012, Bon, et al.
U.S. Appl. No. 13/711,891, filed Dec. 12, 2012, Friesz.
U.S. Appl. No. 13/537,930—Non Final Office Action dated Mar. 14, 2013.

* cited by examiner

*Primary Examiner* — Golam M M Shameem
(74) *Attorney, Agent, or Firm* — Kelly L. Bender

(57) ABSTRACT

The subject of the present invention is a novel process for the preparation of N-[2-n-butyl-3-{4-[(3-dibutylamino)propoxy]benzoyl}-1-benzofuran-5-yl]methanesulfonamide of formula I:

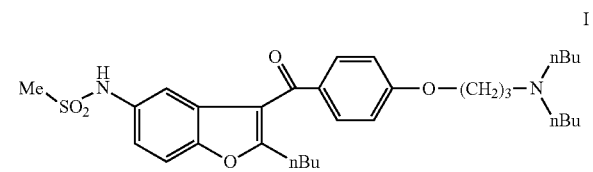

and the new intermediates of the preparation process.

31 Claims, No Drawings

PROCESS FOR THE PREPARATION OF DRONEDARONE

The present invention relates to novel process for the preparation of the N-[2-n-butyl-3-{4-[(3-dibutylamino)-propoxy]benzoyl}-1-benzofuran-5-yl]methane-sulfonamide (dronedarone) of formula I and its pharmaceutically acceptable salts, and to the new intermediates of the preparation process.

I

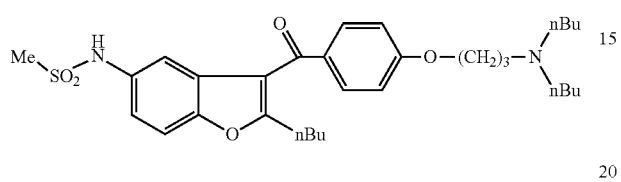

Dronedarone of formula I is used in the treatment of certain pathological changes of the cardiovascular system, especially in the treatment of angina pectoris, high blood pressure, arrhythmia and insufficient cerebral blood circulation (EP 0471609 B1).

There are several known methods for the preparation of dronedarone of formula I. One prior art process (EP 0471609 B1) reacts 2-hydroxy-5-nitro-benzylbromide (VII)

VII

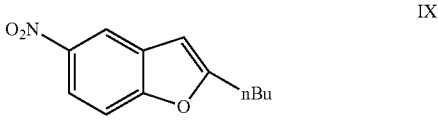

with triphenylphosphine, and the thus obtained 2-hydroxy-5-nitro-benzyl-triphenyl-phosphonium bromide (VIII)

VIII is reacted with pentanoyl chloride to give 2-n-butyl-5-nitro-benzofuran (IX)

IX

Treatment of IX with anisoyl chloride under Friedel-Crafts conditions gives 2-n-butyl-3-(4-methoxy-benzoyl)-5-nitro-benzofuran (X)

X

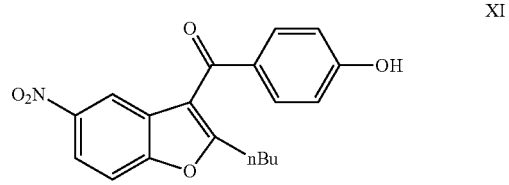

which is heated in the presence of aluminum chloride to obtain 2-n-butyl-3-(4-hydroxy-benzoyl)-5-nitro-benzofuran (XI)

XI

Industrial application of this last reaction step involves difficulties, because 2-n-butyl-3-(4-methoxybenzoyl)-5-nitro-benzofuran (X) is mutagenic, and aluminum chloride is harmful for the health. The resulting 2-n-butyl-3-(4-hydroxy-benzoyl)-5-nitro-benzofuran (XI) on reaction with dibutylamino-propylchloride furnishes 2-n-butyl-3-[4-(3-dibutylamino-propoxy)benzoyl]-5-nitro-benzofuran (XII)

XII

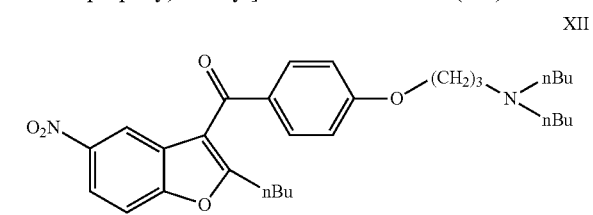

which is reduced in the presence of platinum oxide catalyst to the 5-amino-2-n-butyl-3-[4-(3-dibutylamino-propoxy)benzoyl]benzofuran (XIII).

XIII

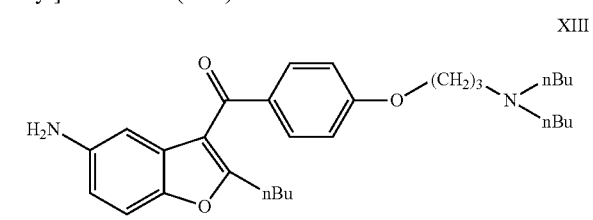

Finally XIII is mesylated, to give dronedarone (I).

This is a linear synthesis, where the desired molecule is built up stepwise, using more and more complicated molecules in the next steps.

Another prior art method for the preparation of dronedarone of formula I is described in the patent application of publication number WO 02/48078. In this method 2-n-butyl-5-nitro-benzofuran (IX) is reacted with 4-[3-(dibutylamino)-propoxy]benzoyl chloride (XIV) under Friedel-Crafts conditions

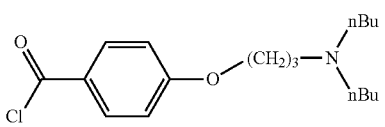

and the thus obtained 2-n-butyl-3-[4-(3-dibutylamino-propoxy)benzoyl]-5-nitro-benzofuran (XII) is reduced in the presence of platinum oxide catalyst to the 5-amino-2-n-butyl-3-[4-(3-dibutylamino-propoxy)benzoyl]benzofuran (XIII).

Mesylation of the latter gives dronedarone (I). In the course of the last, mesylation step, however, a double mesylated derivative is also formed, the yield is low and the purification of dronedarone by column chromatography is complicated. The industrial application of the method is therefore not economical.

The third known method for the preparation of dronedarone (I) is disclosed in patent application of publication number WO 02/48132. This super-convergent method contains the following steps:

5-amino-2-n-butyl-benzofuran (XV)

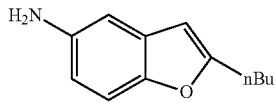

is mesylated and the resulting 2-n-butyl-5-mesylamino-benzofuran (III)

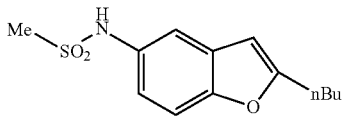

is reacted with 4-[3-(dibutylamino)propoxy]benzoyl chloride hydrochloride salt (XIVa)

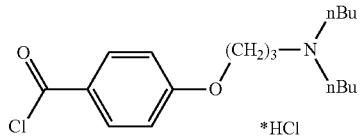

under Friedel-Crafts conditions, to obtain the hydrochloride salt of dronedarone (Ia).

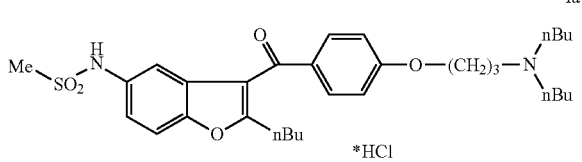

In this method the order of the reaction steps is changed, the reduction step and the mesylation are at the beginning of the synthesis.

This method is very simple and economical regarding the number of the reaction steps. Its drawback is, however, that in the last step the hydrochloride salt of dronedarone is obtained in a substantially contaminated form. This can be explained by the presence of the dibutylamino-propyl group in the Friedel-Crafts reaction. In the published examples the yield is 90%, during the purification steps first the raw dronedarone hydrochloride, then, following treatment with hydrogen chloride solution in isopropanol, the purified dronedarone hydrochloride is obtained (90%).

Another drawback of the method is that the reactants used in the Friedel-Crafts reaction and the obtained by-products are insoluble in water, thus they cannot be removed from the system by aqueous washing.

Our aim was to work out a novel method for the preparation of dronedarone and its pharmaceutically acceptable salts, which method avoids the above mentioned disadvantages, and is economical and industrially applicable.

We have found that if a benzofuran derivative of the general formula (II)

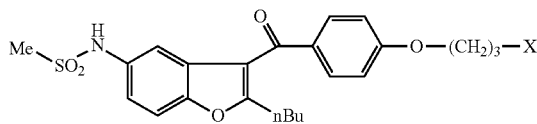

—wherein X stands for chloro-, bromo- or iodo atom, hydroxyl- or activated hydroxyl group—is reacted with dibutylamine, and optionally transformed into its salts, then this method avoids the disadvantages of the processes mentioned before, it is economical and also suitable for industrial application.

One reactant is dibutylamine, which is volatile and thus can be removed from the system and reused after workup, the other is a compound of the general formula (II)—where the meaning of X is as defined above—which can be treated well under the applied reaction conditions. By choosing suitable reaction conditions, dronedarone of formula (I) is obtained in appropriate purity and yield, no by-product is formed, only a few percent of the unreacted starting material may remain in the reaction mixture, and this can be reused.

According to our invention the reaction of the compound of the general formula (II)—wherein X stands for chloro-, bromo- or iodo atom, hydroxyl- or activated hydroxyl group—with dibutylamine is carried out using equivalent amount or excess of dibutylamine. The reaction is performed in an organic solvent or in a mixture of organic solvents. For organic solvent, ketones (acetone, methyl ethyl ketone), for mixture of organic solvents, mixtures of ketones and aromatic hydrocarbons (xylene, toluene) are used. Optionally other organic solvents and their mixtures can also be used.

According to our invention the compound of the general formula (II)—where the meaning of X is as defined above—is reacted with dibutylamine, optionally in the presence of a catalyst. If in the general formula (II) the meaning of X is chloro- or bromo atom, then iodides (as for example sodium iodide or potassium iodide) are used as catalyst. If in the general formula (II) the meaning of X is hydroxyl group, then [Ru(p-cymene)Cl$_2$]$_2$ and 1,1'-bis-(diphenylphosphino)ferrocene or [Ru(p-cymene)Cl$_2$]$_2$ and bis-(2-diphenylphosphinophenyl)ester compounds are used. If in the general formula (II) the meaning of X is iodo atom or activated hydroxyl group, then no catalyst is used.

The reaction of the compound of the general formula (II)—wherein X stands for chloro-, bromo- or iodo atom, hydroxyl- or activated hydroxyl group—with dibutylamine is carried out at the boiling point of the applied solvents or between 60-120° C.

In the compounds of the general formula (II) the hydroxyl group may be activated with methylsulfonyl or substituted benzenesulfonyl group. The substituent of the benzenesulfonyl group may be $C_{1-4}$-alkyl group, halogen atom or nitro group.

According to one embodiment of our invention the 2-n-butyl-5-mesylamino-benzofuran (III)

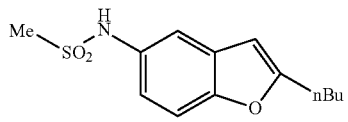

III is reacted with an acid halide of the general formula (IV)

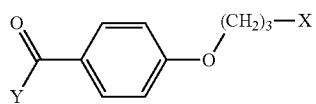

IV where
Y stands for chloro- or bromo atom, X represents halogen atom or protected hydroxyl group, and the thus obtained compound of formula (II)—where the meanings of X are defined above—is reacted with dibutylamine in a manner as described above, to obtain dronedarone of formula (I).

According to our invention the reaction of the benzofuran derivative of formula (III) with the acid halide of the general formula (IV)—where the meanings of X and Y are as defined above—is carried out in the presence of Friedel-Crafts catalyst in a halogenated organic solvent or in nitrobenzene.

The reaction of the compounds (III) and (IV) is carried out in a temperature range of 10-80° C.

According to another embodiment of the invention, a compound of the general formula t (VI),

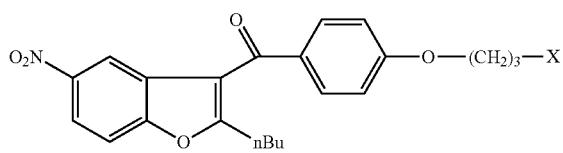

VI wherein X represents chloro-, bromo- or iodo atom, hydroxyl- or activated hydroxyl group, is subjected to hydrogenation reaction and the thus obtained compound of the general formula (V)

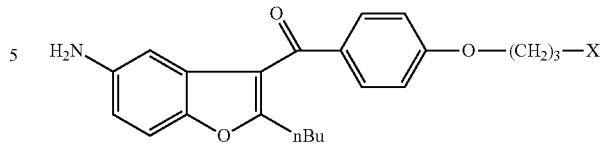

V wherein X represents chloro-, bromo- or iodo atom, hydroxyl- or activated hydroxyl group, is mesylated and the resulting compound of formula (II) is reacted in the above described manner with dibutylamine, to give dronedarone of formula (I).

The hydrogenation reaction of the compound of formula (VI) is carried out in the presence of a catalyst. In one version of the method palladium catalyst is used. In another version of the method platinum catalyst is applied. The hydrogenation reaction of the compound of formula (VI) is performed in an organic solvent, in a temperature range of 10-80° C.

The mesylation of the compound of formula (V) is carried out with methanesulfonyl chloride or with methanesulfonic anhydride. The mesylation of the compound of formula (V) is performed in an inert solvent. According to one preferred embodiment of the reaction, ether or a halogenated solvent is used. The mesylation of the compound of formula (V) is carried out in a temperature range of 5-80° C. The mesylation of the compound of formula (V) is carried out in the presence of a base. According to one preferred embodiment of the reaction an amine (pyridine, triethylamine) is used as base.

The benzofuran derivatives of the general formula (II)

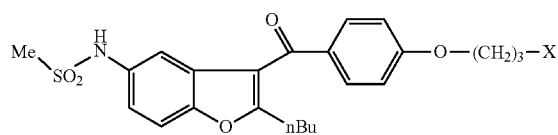

II where X stands for chloro-, bromo- or iodo atom, hydroxyl- or activated hydroxyl group;

the benzofuran derivatives of the general formula (V),

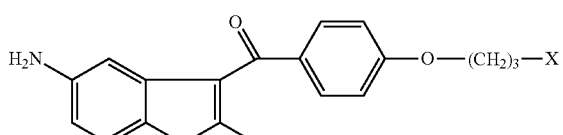

V wherein X stands for chloro-, bromo- or iodo atom, hydroxyl- or activated hydroxyl group;

and
the benzofuran derivatives of the general formula (VI),

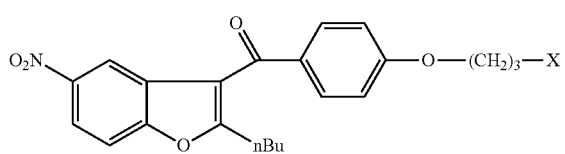

wherein X stands for chloro-, bromo- or iodo atom, hydroxyl- or activated hydroxyl group are new compounds, not known from the literature.

In one embodiment of the present invention the compounds of the general formula (II), where the meanings of X are defined above, are prepared by reacting the compounds of formula (III) with the compounds of the general formula (IV)—wherein Y stands for chloro- or bromo atom, and X represents a halogen atom or a protected hydroxyl group. The compound of formula (III) 15 known, its preparation by mesylation of 5-amino-2-n-butyl-benzofuran is described in patent application WO 02/048132. The compounds of the general formula (IV) wherein the meanings of X and Y are defined above, are also known from the literature, their preparation is disclosed in patent EP 0471609 B1.

In another embodiment of the present invention the compounds of the general formula (II)—where the meaning of X is defined above—are prepared by mesylation of a compound of the general formula (V)—wherein X means chloro-, bromo- or iodo atom, hydroxyl- or activated hydroxyl group. The compound of the general formula (V)—where the meaning of X is defined above—is prepared by catalytic hydrogenation of the benzofuran derivative of the general formula (VI)—where the meaning of X is defined above. The compound of the general formula (VI), wherein X represents bromo atom, is known from the literature. The compound itself, and its preparations are disclosed by the Applicant in patent EP 0471609 B 1. The preparation of the compounds of the general formula (VI)—wherein X means chloro-, bromo- or iodo atom, hydroxyl- or activated hydroxyl group—from the benzofuran derivative (XI), is carried out by analogy of the method described in EP 0471609 B1.

Further details of the invention are demonstrated by the following examples, without limiting the claims to examples.

EXAMPLE 1

(2-n-butyl-5-nitro-1-benzofuran-3-yl)-[4-(3-chloro-propoxy)phenyl]methanone, compound of the general formula (VI) wherein X is chloro atom 40 g (2-n-butyl-3-(4-hydroxybenzoyl)-5-nitro-benzofuran (XI) was dissolved in 320 ml methyl ethyl ketone and to the solution 48.9 g potassium carbonate was added. During stirring 37.2 g 1-bromo-3-chloropropane was added and the mixture was heated to reflux (81-82° C.) and stirred at that temperature for 4 hours. After cooling, the solid salt was filtered off and washed with 3×20 ml methyl ethyl ketone. The filtrate was evaporated. The removed methyl ethyl ketone which contains the excess of 1-bromo-3-chloropropane is used in the next reaction.

Mass of the product: 44.93 g. (99.1%)
Purity (HPLC): 98.9%
Molecular weight: (calculated): 416.1265 Da
(measured): 416.1274 Da $^1$H NMR (DMSO): 0.84 ppm (t, J=7.4 Hz, 3H); 1.27 ppm (6', 2H); 1.72 ppm (5', 2H); 2.26 ppm (5', J=6.5 Hz, 2H); 2.88 ppm (t, J=6.5 HZ, 2H); 3.86 ppm (t, J=6.5 Hz, 2H); 4.26 ppm (t, J=6.0 Hz; 2H); 7.17 ppm (d, J=8.8 Hz, 2H); 7.86 ppm (d, J=8.7 Hz, 2H); 7.96 ppm (m, 1H); 8.29 ppm (m, 1+1H)

EXAMPLE 2

(5-Amino-2-n-butyl-benzofuran-3-yl)-[4-(3-chloro-propoxy)phenyl]methanone, compound of the general formula (V) wherein X is chloro atom Into a 500 ml hydrogenation reactor equipped with turbo stirrer were added 93.8 g (2-n-butyl-5-nitro-1-benzofuran-3-yl)-[4-(3-chloro-propoxy)phenyl]-methanone—the compound of the general formula (VI), where X is chloro atom—and 470 ml abs. ethanol, and then 4.9 g 10% palladium on carbon catalyst. The reaction mixture was heated to 50° C. under stirring at a speed of 800 rotation/minute. Under cooling, hydrogen under 5 bar pressure was set to the reactor and the mixture was stirred at that pressure and temperature for 2 hours. After cooling the catalyst was filtered off and the solvent was removed.

Mass of product: 85.46 g (98%).
Purity (HPLC): 93.8%
Molecular weight: (calculated): 386.1523 Da
(measured): 386.1524 Da $^1$H NMR (DMSO): 0.82 ppm (t, J=7.4 Hz, 3H); 1.24 ppm (6', 2H); 1.64 ppm (5', 2H); 2.22 ppm (5', 2H); 2.75 ppm (t, J=7.6 Hz, 2H); 3.78 ppm (t, J=6.4 Hz, 2H); 4.9 ppm (t, J=5.9 Hz, 2H); 6.62 ppm (d, J=2.3 Hz, 1H); 6.65 ppm (dd, J=8.7; 2.3 Hz, 1H); 7.05 ppm (d, J=8.6 Hz, 2H); 7.22 ppm (d, J=8.7 Hz, 1H); 7.77 ppm (d, J=8.7 Hz, 2H)

EXAMPLE 3

(5-Amino-2-n-butyl-benzofuran-3-yl)-[4-(3-bromo-propoxy)phenyl]methanone, compound of the general formula (V) wherein X is bromo atom The process as described in Example 2 was followed, starting from (2-n-butyl-5-nitro-1-benzofuran-3-yl)-[4-(3-bromopropoxy)phenyl]methanone—the compound of the general formula (VI) where X is bromo atom.

Yield of the product: 97.6%
Purity (HPLC): 92.4%
Molecular weight: (calculated): 430.1018 Da
(measured): 430.1032 Da $^1$H NMR (DMSO): 0.83 ppm (t, J=6.8 Hz, 3H); 1.26 ppm (t, J=6.8 Hz, 2H); 1.69 ppm (m, 2H); 2.25 ppm (m, 1H); 2.33 ppm (m, 1H); 2.84 ppm (m, 2H); 3.72 ppm (m, 1H); 3.86 ppm (m, 1H); 4.25 ppm (m, 2H); 7.15 ppm (d, J=8.1 Hz, 2H); 7.39 ppm (d, 8.1 Hz, 1H); 7.51 ppm (S, 1H); 7.82 ppm (d, J=8.1 Hz, 3H)

EXAMPLE 4

N-(2-n-butyl-3-[4-(3-chloropropoxy)benzoyl]benzofuran-5-yl)methane sulfonamide, compound of the general formula (II) wherein X is chloro atom 8.7 g (5-amino-2-n-butyl-benzofuran-3-yl)-[4-(3-chloro-propoxy)phenyl]methanone—the compound of the general formula (V) wherein X is chloro atom—was stirred in 90 ml dichloromethane until complete dissolution. The solution was cooled to 15° C. and keeping this temperature 1.8 g pyridine, then dropwise, at 15° C., in 15 minutes 2.6 g methanesulfonyl chloride were added. After checking the reaction mixture by HPLC, further 0.19 g pyridine and 0.26 g methanesulfonyl chloride were added and stirring was continued for 30 minutes. The reaction mixture was washed with 2×20 ml water, 2×20 ml 5% hydrochloric acid, and 2×20 ml 5% NaHCO$_3$ solution, and then it was evaporated.

Mass of the product: 10.1 g (96.6%)

Purity: 87.5%

Following crystallisation from abs. ethanol (yield 72%), the purity (by HPLC) of the product: 100%

Melting point: 109.7-110.3° C.

$^1$H NMR (DMSO-D6): 9.61 ppm (1H), 7.82 ppm (J=8.7 Hz, 2H), 7.65 ppm (d, 1H), 7.31 ppm (dd, J=2.1 Hz, 1H), 7.24 ppm (dd, J=8.8 Hz, 1H), 7.14 ppm (2H), 4.25 ppm (t, J=6.0 Hz, 2H), 3.85 ppm (t, J=6.4 Hz, 2H), 2.92 ppm (S, 2H), 2.84 ppm (t, J=7.5 Hz, 2H), 2.25 ppm (m, 2H), 1.69 ppm (m, 2H), 1.28 ppm (m, 2H), 0.84 ppm (t, J=7.3 Hz, 3H)

EXAMPLE 5

N-(2-n-butyl-3-[4-(3-bromopropoxy)-benzoyl]benzofuran-5-yl)methanesulfonamide, compound of the general formula (II) where X is bromo atom The process as described in Example 4 was followed, starting from (5-amino-2-n-butyl-benzofuran-3-yl)-[4-(3-bromopropoxy)phenyl]methanone—the compound of the general formula (V) where X is bromo atom.

Yield of the product: 95.8%

Purity: 86.8% (HPLC)

Molecular weight: (calculated): 508.0793 Da (measured): 508.0780 Da $^1$H NMR (DMSO): 0.84 ppm (t, J=7.3 Hz, 3H); 1.26 ppm (6', 2H); 1.69 ppm (5', 2H); 2.33 ppm (5', 2H); 2.84 ppm (t, J=6.5 Hz, 2H); 2.92 ppm (s, 3H); 3.73 ppm (t, J=6.5 Hz, 2H); 4.23 ppm (t, J=6.0 Hz, 2H); 7.14 ppm (d, J=8.8 Hz, 2H); 7.23 ppm (dd, J=8.9; 2.3 Hz, 1H, 7.25 ppm (d, J=2.1 Hz, 1H, 7.66 ppm (d, J=8.8 Hz, 1H, 7.82 ppm (d, J=8.8 Hz, 2H)

EXAMPLE 6

N-(2-n-butyl-3-[4-(3-chloropropoxy)benzoyl]benzofuran-5-yl)methanesulfonamide, compound of the general formula (II), where X is chloro atom 5.2 g 2-n-butyl-5-mesylamino-benzofuran (III) was mixed with 30 ml dichloromethane and to the resulting suspension 5.55 g 4-(3-chloropropoxy)benzoic acid chloride—the compound of the general formula (IV), where X and Y are chloro atom—was slowly added. The reaction mixture was cooled to 5° C. and in 15 minutes, in four portions 3.89 g iron(III) chloride was added, keeping the temperature between 5-10° C. The mixture was stirred at 20° C. for 1 hour, then heated to 40-45° C. and in 30 minutes 54 ml water was added. The mixture was stirred at that temperature for 30 minutes. The phases were, still warm, separated. The dichloromethane phase was washed by stirring with 2×16 ml 5% NaHCO$_3$ solution, then with 2×16 ml water. The solvent was removed by evaporation.

Mass of the product: 9.13 g (98.4%)

Purity (HPLC) 89.6%.

After crystallisation (88%) from abs. ethanol, the purity of the product (by HPLC): 100%

Melting point: 109.8-110.2° C.

The product is identical with the product prepared in Example 4.

EXAMPLE 7

N-(2-n-butyl-3-[4-(3-chloropropoxy)benzoyl]benzofuran-5-yl)methanesulfonamide, compound of the general formula (II), where X is chloro atom The reaction was performed as described in Example 6, but chlorobenzene was used as solvent, instead of dichloromethane.

Mass of the product: 97.6%

Purity (HPLC): 88.6%

EXAMPLE 8

N-(2-n-butyl-3-[4-(3-chloropropoxy)benzoyl]benzofuran-5-yl)methanesulfonamide, compound of the general formula (II), where X is chloro atom The reaction was performed as described in Example 7, but aluminum chloride was used instead of iron(III) chloride.

Yield of the product: 96.8%

Purity (HPLC): 86.5%

EXAMPLE 9

N-(2-n-butyl-3-[4-(3-bromopropoxy)benzoyl]benzofuran-5-yl)methanesulfonamide, the compound of the general formula (II), where X is bromo atom To the suspension of 5 g 2-n-butyl-5-mesylamino-benzofuran (III) in 35 ml dichloromethane was slowly added 5.19 g 4-(3-bromopropoxy)benzoyl chloride—the compound of the general formula (IV), where X is bromo atom and Y is chloro atom. The reaction mixture was cooled to 5° C. and in 20 minutes, in five portions 9 g iron(III) chloride was added, maintaining the temperature between 5-10° C. The mixture was stirred at 20° C. for 1 hour, then heated to 40-45° C., and in 30 minutes 55 ml water was added. The mixture was stirred at that temperature for 40 minutes.

The phases were, still warm, separated. The dichloromethane phase was washed by stirring with 2×16 ml 5% NaHCO$_3$ solution, then with 2×16 ml water. The solvent was removed by evaporation.

Mass of the product: 8.1 g (93.4%)

Purity (HPLC) 88.2%.

The product is identical with the product prepared in Example 5.

EXAMPLE 10

N-(2-n-butyl-3-[4-(3-bromopropoxy)benzoyl]benzofuran-5-yl)methanesulfonamide, the compound of the general formula (II), where X is bromo atom The reaction was performed as described in Example 9, but chlorobenzene was used as solvent, instead of dichloromethane.

Mass of the product: 7.9 g

Purity (HPLC): 86.7%

EXAMPLE 11

N-(2-n-butyl-3-[4-(3-bromopropoxy)benzoyl]benzo-
furan-5-yl)methanesulfonamide, the compound of
the general formula (II), where X is bromo atom The reaction was performed as described in Example 9, but aluminum chloride catalyst was used, instead of iron(III) chloride
Mass of the product: 8.0 g
Purity (HPLC): 85.6%

EXAMPLE 12

N-[2-n-butyl-3-{4-[(3-dibutylamino)propoxy]ben-
zoyl}-1-benzofuran-5-yl]-methanesulfonamide, the
compound of the general formula (I)

5 g N-(2-n-butyl-3-[4-(3-chloropropoxy)benzoyl]benzo-furan-5-yl)-methanesulfonamide—the compound of the general formula (II), where X is chloro atom—was dissolved in 90 ml methyl ethyl ketone, then 16.7 g dibutylamine and 6.46 g sodium iodide were added and the mixture was stirred for 16 hours. The reaction mixture was evaporated, 100 ml dichloromethane and 100 ml water were added. The phases were separated. The organic phase was washed by stirring with 50 ml 5% hydrochloric acid, then with 50 ml water. The solvent was distilled off. The dibutylamine recovered from the solvent was used in a next reaction.
Mass of the product: 5.9 g (100.0%)
Purity (HPLC): 98.7%
The product is purified through its oxalate salt (90%).
Purity of the oxalate salt (HPLC): 100%
$^1$H NMR (DMSO): 0.8-0.9 ppm (m, 9H); 1.2-1.5 ppm (m, 10H); 1.67 ppm (5', 2H); 1.87 ppm (5', 2H); 2.38 ppm (t, J=7.2 Hz, 4H); 2.57 ppm (m, 2H); 2.81 ppm (t, J=7.5 Hz, 2H); 2.91 ppm (s, 3H); 9.51 ppm (t, J=6.2 Hz, 2H); 7.09 ppm (d, J=8.8 Hz, 2H); 7.24 ppm (dd, J=8.9; 2.2 Hz, 1H); 7.38 ppm (d, J=2.1 Hz, 1H); 7.65 ppm (d, J=8.8 Hz, 1H); 7.81 ppm (d, J=8.8 Hz, 2H)

EXAMPLE 13

N-[2-n-butyl-3-{4-[(3-dibutylamino)propoxy]ben-
zoyl}-1-benzofuran-5-yl]-methanesulfonamide, the
compound of the general formula (I)

The reaction was performed as described in Example 12, but potassium iodide was used, instead of sodium iodide.
Mass of the product: 100.0%
Purity (HPLC): 97.8%

EXAMPLE 14

N-[2-n-butyl-3-{4-[(3-dibutylamino)propoxy]ben-
zoyl}-1-benzofuran-5-yl]-methanesulfonamide, the
compound of the general formula (I)

The reaction was performed as described in Example 12, but acetone was used, instead of methyl ethyl ketone.
Mass of the product: 98.7%
Purity (HPLC): 97.1%

EXAMPLE 15

N-[2-n-butyl-3-{4-[(3-dibutylamino)propoxy]ben-
zoyl}-1-benzofuran-5-yl]-methanesulfonamide, the
compound of the general formula (I)

The reaction was performed as described in Example 12, but for solvent, a 9:1 mixture of methyl ethyl ketone and toluene was used.
Yield of the product: 98.8%
Purity (HPLC): 98.7%

EXAMPLE 16

N-[2-n-butyl-3-{4-[(3-dibutylamino)propoxy]ben-
zoyl}-1-benzofuran-5-yl]-methanesulfonamide, the
compound of the general formula (I)

The reaction was performed as described in Example 12, using N-(2-n-butyl-3-[4-(3-bromopropoxy)benzoyl]benzo-furan-5-yl)methanesulfonamide—the compound of the general formula (II), where X is bromo atom—for starting material.
Yield of the product: 98.7%
Purity (HPLC): 97.7%
The product is identical with the product prepared in Example 12.

EXAMPLE 17

N-[2-n-butyl-3-{4-[(3-dibutylamino)propoxy]ben-
zoyl}-1-benzofuran-5-yl]-methanesulfonamide, the
compound of the general formula (I)

The reaction was performed as described in Example 12, with the difference that the starting material was N-(2-n-butyl-3-[4-(3-methanesulfonyloxy-propoxy)benzoyl]benzo-furan-5-yl)methanesulfonamide—the compound of the general formula (II), where X is methanesulfonyloxy group—and sodium iodide was not used.
Yield of the product: 89.1%
Purity (HPLC): 98.1%

EXAMPLE 18

N-[2-n-butyl-3-{4-[(3-dibutylamino)propoxy]ben-
zoyl}-1-benzofuran-5-yl]-methanesulfonamide, the
compound of the general formula (I)

The reaction was performed as described in Example 12, with the difference that the starting material was N-(2-n-butyl-3-[4-(3-tosyloxy-propoxy)benzoyl]benzofuran-5-yl)-methanesulfonamide—the compound of the general formula (II), where X is tosyloxy group—and sodium iodide was not used.
Yield of the product: 97.81%
Purity (HPLC): 97.6%

EXAMPLE 19

N-[2-n-butyl-3-{4-[(3-dibutylamino)propoxy]ben-
zoyl}-1-benzofuran-5-yl]-methanesulfonamide, the
compound of the general formula (I)

0.5 g N-(2-n-butyl-3-[4-(3-hydroxy-propoxy)-benzoyl]-benzofuran-5-yl)-methanesulfonamide—the compound of the general formula (II), where X is hydroxyl group—was dissolved in 8 ml toluene. To the solution 1.5 g dibutylamine and 1.2 mol % [Ru(p-cymene)Cl$_2$]$_2$ and 2.5 mol % 1,1'-bis-(diphenylphosphino)-ferrocene catalysts were added and the reaction mixture was kept under reflux for 24 hours. The solvent was removed by evaporation, the residue was taken up in 10 ml dichloromethane and washed by stirring with 5 ml 1% hydrochloric acid, then with 10 ml water. The solvent was removed by evaporation.

Mass of the product: 0.51 g (82.5%)
Purity (HPLC): 92.4%

The product is identical with the product prepared according to Example 12.

EXAMPLE 20

N-[2-n-butyl-3-{4-[(3-dibutylamino)propoxy]benzoyl}-1-benzofuran-5-yl]-methanesulfonamide hydrogen chloride salt, the compound of the general formula (Ia)

5 g dronedarone base was dissolved in 24 ml isopropanol and 0.98 g 37% hydrochloric acid was added to it. The mixture was cooled to 0° C. and kept at that temperature for 5 hours. The precipitated white crystals were collected, washed with 3.5 ml isopropanol. The product was dried at 50° C. under vacuum.

Mass of the product: 5.2 g (97.6%)
Purity (HPLC): 100%

What is claimed is:

1. A process for the preparation of N-[2-n-butyl-3-{4-[(3-dibutylamino)propoxy]benzoyl}-1-benzofuran-5-yl]methanesulfonamide of formula I:

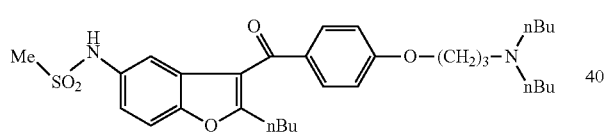

I or a pharmaceutically acceptable salt thereof, comprising reacting a benzofuran derivative of formula II:

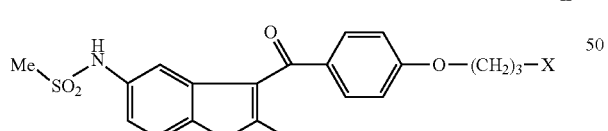

II wherein X represents chloro-, bromo- or iodo atom, hydroxyl- or activated hydroxyl group; with dibutylamine; and, optionally, forming the salt of the product.

2. The process according to claim 1, comprising carrying out the reaction with excess dibutylamine.

3. The process according to claim 1, comprising carrying out the reaction in an organic solvent or in a mixture of organic solvents.

4. The process according to claim 3, wherein the organic solvent is selected from ketones.

5. The process according to claim 4, wherein the ketone is acetone or methyl ethyl ketone.

6. The process according to claim 3, wherein the mixture of organic solvents is a mixture of a ketone and aromatic hydrocarbon.

7. The process according to claim 6, wherein the aromatic hydrocarbon is toluene or xylene.

8. The process according to claim 1, wherein, for the benzofuran derivative of formula II, the meaning of X is chloro- or bromo atom or hydroxyl group; said method comprising carrying out the reaction in the presence of a catalyst.

9. The process according to 8, wherein, for the benzofuran derivative of formula II, the meaning of X is chloro- or bromo atom; and the catalyst is sodium- or potassium iodide.

10. The process according to claim 8, wherein for the benzofuran derivative of formula II, the meaning of X is hydroxyl group, and the catalysts are [Ru(p-cymene)Cl$_2$]$_2$ and 1,1'-bis-(diphenylphosphino)ferrocene or the catalysts are [Ru(p-cymene)Cl$_2$]$_2$ and bis-(2-diphenylphosphinophenyl)-ester.

11. The process according to claim 1, comprising carrying out the reaction at the boiling point of the solvents or at a temperature between 60 and 120° C.

12. The process according to claim 1, wherein for the benzofuran derivative of formula II, the meaning of X is activated hydroxyl group, and the activating group is mesyloxy- or substituted benzenesulfonyloxy group.

13. The process according to claim 12, wherein the substituents of the substituted benzenesulfonyloxy group are selected from methyl group, nitro group and halogen atom.

14. The process according to claim 1, further comprising reacting the benzofuran derivative of formula III:

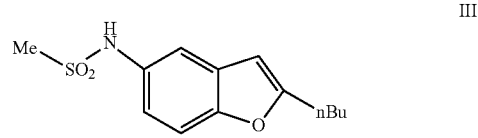

III with a benzoyl halogenide of formula IV:

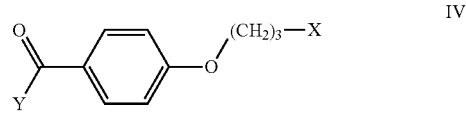

IV wherein Y represents chloro- or bromo atom, X represents halogen atom or protected hydroxyl group; and reacting the resulting benzofuran derivative of formula II:

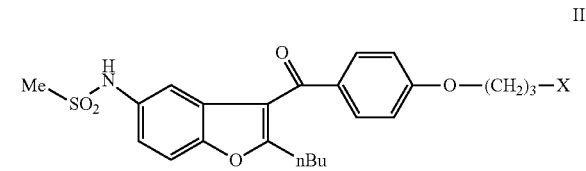

II wherein X is as defined in claim 1, with dibutylamine; and, optionally, forming the salt of the product.

15. The process according to claim 14, comprising carrying out the reaction of the compound of formula III with the compound of formula IV in the presence of a Friedel-Crafts catalyst.

16. The process according to claim 15, wherein the Friedel-Crafts catalyst is aluminum chloride or iron(III) chloride.

17. The process according to claim 14, comprising carrying out the reaction of the compound of formula III with the compound of formula IV in a halogenated solvent.

18. The process according to claim 17, wherein the halogenated solvent is selected from dichloromethane, dichloroethane and chlorobenzene.

19. The process according to claim 14, comprising carrying out the reaction of the compound of formula III with the compound of formula IV in nitrobenzene.

20. The process according to claim 14, comprising carrying out the reaction of the compound of formula III with the compound of formula IV at a temperature between 10 and 80° C.

21. The process according to claim 1, comprising:
a) subjecting a compound of formula VI:

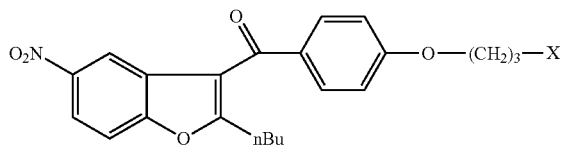

VI wherein X represents chloro-, bromo- or iodo atom, hydroxyl- or activated hydroxyl group,
to a hydrogenation reaction;
and
b) mesylating the resulting compound of formula V:

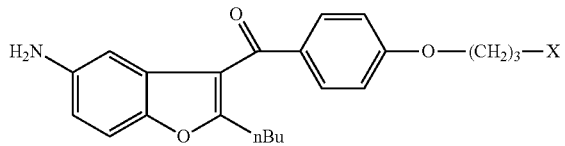

V wherein X represents chloro-, bromo- or iodo atom, hydroxyl- or activated hydroxyl group;
and
c) reacting the resulting benzofuran derivative of formula II:

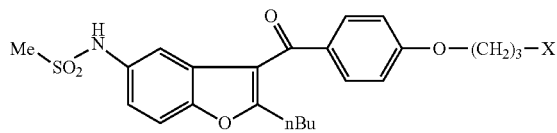

II wherein X represents chloro-, bromo- or iodo atom, hydroxyl- or activated hydroxyl group; with dibutylamine; and, optionally, transforming the thus obtained compound of formula I into a salt thereof.

22. The process according to claim 21, comprising carrying out the hydrogenation reaction of step a) in the presence of a catalyst.

23. The process according to claim 22, wherein the catalyst is palladium or platinum.

24. The process according to claim 21, comprising carrying out the reaction step a) in an organic solvent at a temperature between 10 and 80° C.

25. The process according to claim 21, comprising carrying out the reaction step b) using methanesulfonyl chloride or methanesulfonic anhydride as a mesylating agent.

26. The process according to claim 21, comprising carrying out the reaction step b) in an inert solvent.

27. The process according to claim 26, wherein the inert solvent is an ether or halogenated hydrocarbon.

28. The process according to claim 21, comprising carrying out reaction step b) at a temperature between 5 and 80° C.

29. The process according to claim 21, comprising carrying out reaction step b) in the presence of a base.

30. The process according to claim 29, wherein an amine compound is used as a base.

31. The process according to claim 30, wherein the amine is selected from pyridine and triethylamine.

* * * * *

UNITED STATES PATENT AND TRADEMARK OFFICE
CERTIFICATE OF CORRECTION

| | | |
|---|---|---|
| PATENT NO. | : 8,501,971 B2 | Page 1 of 1 |
| APPLICATION NO. | : 13/479615 | |
| DATED | : August 6, 2013 | |
| INVENTOR(S) | : Antal Friesz et al. | |

It is certified that error appears in the above-identified patent and that said Letters Patent is hereby corrected as shown below:

Title Page:

In the Foreign Application Priority Data, item (30), please replace "0900759" with --P0900759--.

In the Abstract, item (57), line 2, please replace "N-[2-n-butyl" with --$N$-[2-$n$-butyl--.

In the Claims:

At column 14, claim 10, line 15, please replace "[Ru(p-cymene)Cl$_2$]$_2$" with --[Ru($p$-cymene)Cl$_2$]$_2$--;

At column 14, claim 10, line 17, please replace "[Ru(p-cymene)Cl$_2$]$_2$" with --[Ru($p$-cymene)Cl$_2$]$_2$--.

Signed and Sealed this
Twenty-fourth Day of November, 2015

Michelle K. Lee
*Director of the United States Patent and Trademark Office*